(12) United States Patent
Vaquero López et al.

(10) Patent No.: US 8,259,899 B2
(45) Date of Patent: Sep. 4, 2012

(54) MULTI-MODALITY TOMOGRAPHY APPARATUS

(75) Inventors: Juan José Vaquero López, Madrid (ES); Manuel Menéndez Desco, Madrid (ES)

(73) Assignee: Fundacion Para la Investigacion Biomedica del Hospital Gregorio Maranon, Madrid (ES)

( * ) Notice: Subject to any disclaimer, the term of this patent is extended or adjusted under 35 U.S.C. 154(b) by 0 days.

(21) Appl. No.: 12/083,739

(22) PCT Filed: Oct. 26, 2006

(86) PCT No.: PCT/ES2006/070160
§ 371 (c)(1), (2), (4) Date: Dec. 11, 2008

(87) PCT Pub. No.: WO2007/048867
PCT Pub. Date: May 3, 2007

(65) Prior Publication Data
US 2009/0213983 A1  Aug. 27, 2009

(30) Foreign Application Priority Data
Oct. 26, 2005  (ES) .................................. 200502612

(51) Int. Cl.
G01N 23/083 (2006.01)
H05G 1/70 (2006.01)
G01T 1/00 (2006.01)
(52) U.S. Cl. ........ 378/9; 378/193; 250/370.09; 250/394
(58) Field of Classification Search ................ 378/4–20, 378/62, 63, 193, 195, 210; 250/363.01, 363.02, 250/363.03, 363.04, 363.08, 366, 370.08, 250/370.09, 394, 395, 363.05
See application file for complete search history.

(56) References Cited

U.S. PATENT DOCUMENTS

| 5,966,422 | A | 10/1999 | Dafni et al. |
| 6,072,851 | A * | 6/2000 | Sivers .............................. 378/15 |
| 6,449,331 | B1 * | 9/2002 | Nutt et al. ........................ 378/19 |
| 6,490,476 | B1 * | 12/2002 | Townsend et al. ............. 600/427 |
| 6,661,866 | B1 * | 12/2003 | Limkeman et al. ............. 378/19 |
| 6,670,614 | B1 * | 12/2003 | Plut et al. .................. 250/363.04 |
| 6,810,103 | B1 | 10/2004 | Tybinkowski et al. |
| 6,956,925 | B1 * | 10/2005 | Hoffman ............................ 378/4 |
| 7,020,233 | B1 | 3/2006 | Tybinkowski et al. |
| 7,412,028 | B2 * | 8/2008 | Altman ........................... 378/63 |
| 2002/0191734 | A1 * | 12/2002 | Kojima et al. ..................... 378/4 |
| 2003/0153828 | A1 * | 8/2003 | Kojima et al. ................ 600/425 |
| 2004/0161076 | A1 * | 8/2004 | Goldstein ..................... 378/160 |
| 2004/0210126 | A1 | 10/2004 | Hajaj et al. |
| 2005/0023471 | A1 * | 2/2005 | Wang et al. .............. 250/363.04 |

(Continued)

FOREIGN PATENT DOCUMENTS
WO  WO 0075691 A1 * 12/2000
WO  03/032829 A1  4/2003

*Primary Examiner* — Anastasia Midkiff
(74) *Attorney, Agent, or Firm* — Ladas & Parry LLP

(57) ABSTRACT

The invention relates to a multi-modality tomography apparatus (11) including a first tomograph (13) and a second tomograph or imaging system (14) using different tomography techniques, such as X-ray CT tomography and PET or SPECT tomography, or a tomographic or planar optical imaging system, which are located on the same face of a support means (12) which can rotate in both directions of rotation around an axial support shaft (12), such that a subject undergoing examination and placed on a subject support does not have to be moved during a tomographic examination with any of the two tomographs (13, 14) installed on the same face of the support (12).

26 Claims, 5 Drawing Sheets

U.S. PATENT DOCUMENTS

| | | |
|---|---|---|
| 2005/0067578 A1 | 3/2005 | Ueno et al. |
| 2006/0050845 A1* | 3/2006 | Juni ................................ 378/51 |
| 2006/0086905 A1* | 4/2006 | Fritzler et al. ........... 250/363.05 |
| 2006/0113482 A1* | 6/2006 | Pelizzari et al. ......... 250/370.09 |

* cited by examiner

MULTI-MODALITY TOMOGRAPHY APPARATUS

FIELD OF THE INVENTION

The present invention relates in general to a multi-modality tomography apparatus that combines several tomography and imaging techniques in one plane of a support ring so that a support for the sample, which can be a living being, is introduced in the mentioned support ring.

STATE OF THE ART

The existence of hybrid or multi-modality tomography apparatuses combining different tomography systems is known from the state of the art, such as X-ray computer assisted tomography (X-ray CT), single photon emission computer assisted tomography (SPECT), and positron emission tomography (PET), and optical imaging in its various modalities, arranged in either two support systems placed in coaxial configuration one after another or arranged on both sides of one support ring.

These diagnostic methods use different techniques and produce different types of anatomical and functional information that is often complementary for both the process of medical diagnosis and biomedical research.

X-ray tomography provides anatomical images in two and/or three dimensions of the body of a subject such as a patient and/or an animal. The X-ray CT involves the use of an X-ray emitter and an X-ray receptor wherein a projection image is normally extracted.

PET tomography involves the detection of collinear gamma rays produced from positron annihilation emitted by some radioactive element that is used for labelling various chemical substances, called tracers or radiopharmaceuticals. Tracers are synthesized from labelled precursors and are administrated to the subject. Consequently, the emitter source is housed in the subject's body and the detector is housed in the support ring.

PET tomographs consist of a large number of scintillation detectors that partially or totally surround a patient or specimen and are connected to data acquisition systems with analog and digital steps. Images of spatial-temporal distributions of administered radiopharmaceutical products are reconstructed using mathematical image reconstruction techniques similar to those applied to X-ray tomography.

SPECT tomographs consist of one or more detector heads that capture gamma photons emitted by gamma emitter radioisotopes that compose a radiopharmaceutical, with less resolution than PET tomographs.

PET and SPECT tomographs allow visualizing and quantifying the function of organs in the subject undergoing examination, i.e. they allow obtaining different types of functional information, in accordance with the tracer used, for example about blood circulation and metabolism, which cannot be easily observed by other technologies.

The optical image is generated from the detection of wavelength photons comprised between ultraviolet and far infrared generated in the sample generally by means of fluorescence, phosphorescence, luminescence or bioluminescence phenomena. These photonic phenomena are originated by the presence of determined substances used for labelling several chemical compounds, called tracers. Tracers are synthesized from precursors and are administrated to the subject. Consequently, the photon emitter source is located in the subject's body and the detector is located in the support ring.

Optical imaging systems based on fluorescence or bioluminescence are widely used in biomedical research due to their reduced cost and high capacity. They are essentially planar systems though some previous attempts of performing tomography exist. These approaches have been relatively successful mainly due to the dispersion and attenuation of light in the biological tissue which considerably limits the tomographic capacity. Current systems are based on CCD type sensors conveniently refrigerated and set up to operate in very low luminosity conditions, arranged in a casing which completely blocks the external light wherein the sample is placed for examination. This sample emits light of different types according to the experimental conditions, and the detector element will capture the photons in a given time interval, thus generating the image. Images of spatial-temporal distributions of the administered pharmaceutical products are presented using different representation techniques.

The known state of the art related to hybrid systems of tomography acquisition has several drawbacks, such as that for visualization of one region of a subject undergoing examination with both tomography techniques, it is necessary to axially move said subject placed on the bed from one tomography system to another. Even in hybrid equipment in which said tomography systems are mounted on a single support ring it is necessary to move the object or subject being examined from one face to the other face of the mentioned support ring, since tomography systems are installed in each face of the support.

Other drawbacks arise from moving the subject undergoing examination, for example the analyzed internal organ/organs can move during said movement, therefore the images no longer perfectly coincide, or all possible connections that are installed on the subject for vital function control, anesthesia, temperature control, etc. have to be moved with the mentioned subject during the movement of same, running the risk that some of them disconnect, so that it is necessary to repeat the tests which are performed on the patient. This problem is increased, for example, in the event that the subject undergoing examination is a small laboratory animal, or in the event that the subject is undergoing surgery, making the movement of same even more difficult.

In the known multi-modality tomography apparatuses, there is not a direct overlapping of the fields of view of each tomographic or planar imaging technique, said overlapping is conducted using post-processing techniques on the three-dimensional data obtained by image tomography systems for the purpose of geometrically co-registering, making the volumes sampled by each of the mentioned tomography devices coincide.

It is therefore necessary to develop a multi-modality tomography apparatus that allows direct overlapping of images, due to the coincidence of fields of view of different tomography techniques, without the necessity to move the subject undergoing examination so as to avoid the drawbacks this involves.

SUMMARY OF THE INVENTION

The present invention aims to solve or reduce one or more of the previously mentioned drawbacks by means of a multi-modality tomography apparatus. Embodiments of the invention are defined in dependent claims.

An object of the present invention is to install at least two tomographic or planar imaging devices using different techniques, such as PET or SPECT tomograph, X-ray CT tomograph, or optical imaging systems in a coplanar configuration on the same face of a support means which can rotate in both directions of rotation, around the axial shaft of the support means. A subject undergoing tomography examination can be placed on a support for the sample or bed being introduced in a concentric hole of the support means before beginning the sampling, so that it is not necessary to move the subject to perform the examination with any of the imaging devices installed on the support.

Another object of the invention is that the sampled three-dimensional space is substantially the same for the imaging systems using different technique, so that the co-registration naturally occurs, and all of it is achieved without having to sacrifice any intrinsic features of each of the tomographs, such that one tomograph does not interfere in the other tomograph or imaging system which simultaneously coexist in the support.

Still another object of the invention is the modular design of each tomograph such that if desired, a tomograph using a first predetermined technique, for example, PET tomograph, is substituted in a simple, fast and convenient manner by a tomograph using a second predetermined technique, such as a SPECT tomograph or an optical imaging device by means of natural or fluorescent light.

Another object of the invention is to place the different tomographic images in orthogonal shafts so as to make it possible to perform simultaneous, sequential imaging or a mixture of both of the same volume of the examined subject.

Still another object of the invention is that the coexistence of tomographs or imaging system using different techniques, i.e. different types of simultaneous radiation in the same field of view, does not induce intermodal interferences of a first tomograph in a second tomograph using a different technique which can saturate the detectors or introduce noise in the second tomograph or vice versa.

Another object of the invention is to prevent exposing an operator who is manipulating the examined subject during the operation of a tomograph, specifically, the X-ray CT tomograph, to ionizing radiations.

Still another object of the invention is to use a minimum number of PET detectors maintaining high sensitivity and spatial resolution.

Another object of the invention is to provide a smaller, more lightweight and reduced-cost multi-modality tomography apparatus that is easy to handle and maintain.

BRIEF DESCRIPTION OF THE FIGURES

A more detailed explanation of the invention is given in the following description based on the appended figures wherein.

DESCRIPTION OF THE INVENTION

Figure 1:
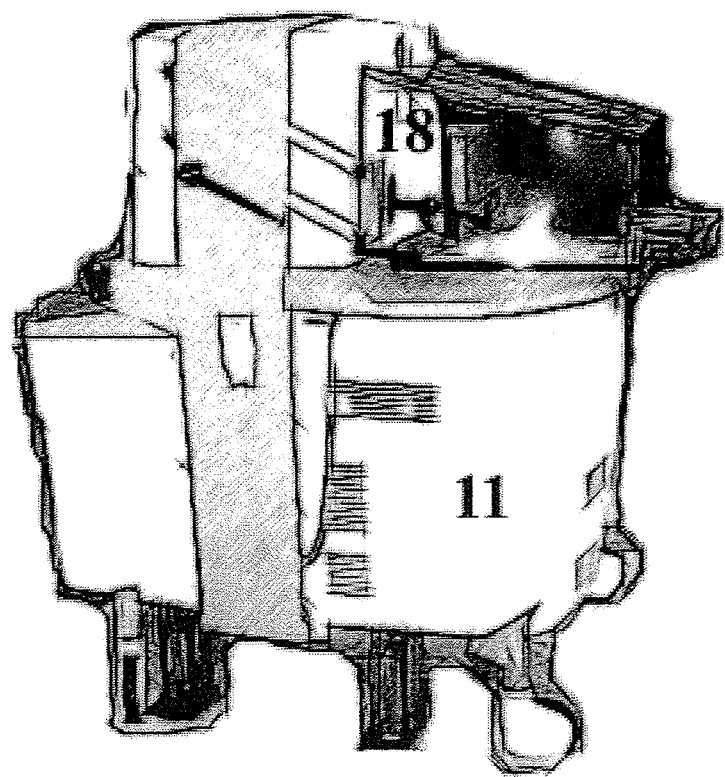
FIG. 1 shows an elevation view of a multi-modality tomography apparatus according to the invention.

In reference to FIG. 1, a multi-modality tomography apparatus 11 is illustrated below combining, for example, the structural information of a first tomograph 13 with the metabolic information of a second tomograph or planar imaging system 14 in a single imaging system.

Tomograph 11 allows the use of at least two different radiation systems in order to obtain images and two-dimensional and three-dimensional reconstructions of spatial distributions of tissue or biochemical properties of same.

Some of the tomography systems that can be installed in tomograph 11 are X-ray tomography, i.e. X-ray CT; positron emission tomograph (PET), single photon emission tomograph (SPECT) or optical imaging, tomographic or projective techniques. For a better explanation of the invention, and by way of example, essentially, it will be considered that possible incipient injuries are detected with the second PET tomograph 14 and are precisely located using the first CT tomograph 13.

Figure 2:
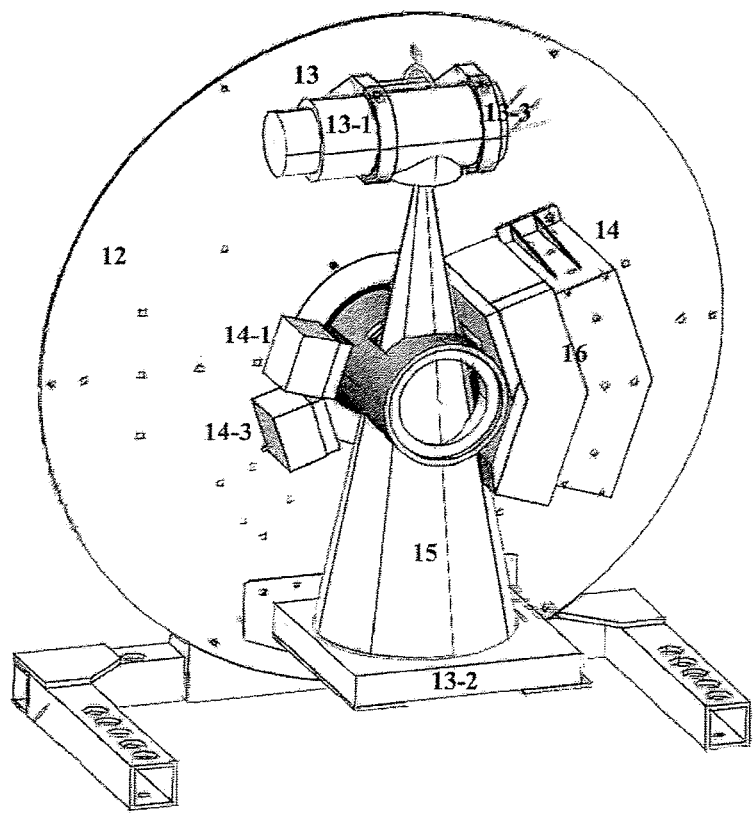
FIG. 2 shows an elevation view of a support ring according to the invention.

In relation to FIG. 2, tomograph 11 comprises a support means 12 or support ring with a hole in the center allowing the movement, along the longitudinal or axial shaft of the support 12, of a substantially planar support means such as bed which is adapted for receiving a subject undergoing examination so that the subject can remain horizontal and still. In this horizontal position the subject is more easily controlled and an operator can more comfortably act on the subject.

Tomograph 11 includes location means (not shown) to place the bed exactly in a predetermined position in the hole of the support 12, before taking any samples, while taking samples by means of any imaging technique, the bed does not move. To sum up, the subject undergoing examination is placed on the bed and after being placed in a precise manner on same, it longitudinally moves until the area of the subject to examine is in the overlapping effective field of view of the different types of tomograph which will take detailed images of the desired area of examination.

As seen in FIG. 2, support 12 can rotate around a horizontal axial shaft which can rotate in both directions. One of the faces of support 12 comprises mechanical securing means (not shown) configured to support and secure in place the components or apparatuses related to the two different computer assisted tomography techniques installed simultaneously and in one plane of support 12, for example, the first X-ray CT tomograph 13, on the ordinate axis and the second PET tomograph 14 on the abscissa axis, to facilitate the registration and subsequent fusion of the images, one functional and another anatomical, produced by both tomographs 14, 13 respectively. Therefore, the first tomograph 13 and the second tomograph 14 are installed on the same plane.

Mechanical securing means are designed such that they facilitate changing the tomography technique, i.e. the design of each tomography or planar imaging technique means is modular, allowing its installation and disassembly in a simple, easy and fast manner.

Electrical signals of the first tomograph 13 and second tomograph 14 are very sensitive to interferences. Given that the support 12 rotates in both clockwise and counterclockwise directions of rotation, the installation of electrical cables for feeding the tomographs 13, 14 and for sending the electrical signals related to the sampling are configured to attenuate a possible noise signal and prevent the reduction of the signal to noise ratio; therefore, transmission of the electrical signal related to the sampling through the mobile cable to an analog/digital converter is not deteriorated.

The first tomograph 13 comprises an emission means 13-1 which emits a cone-shaped beam 15, and X-ray detection means 13-2. In stand by, the emitter 13-1 is located in the upper part of the face of the support 12, and the receptor 13-2 is located in the lower part of the support 12.

Figure 5:
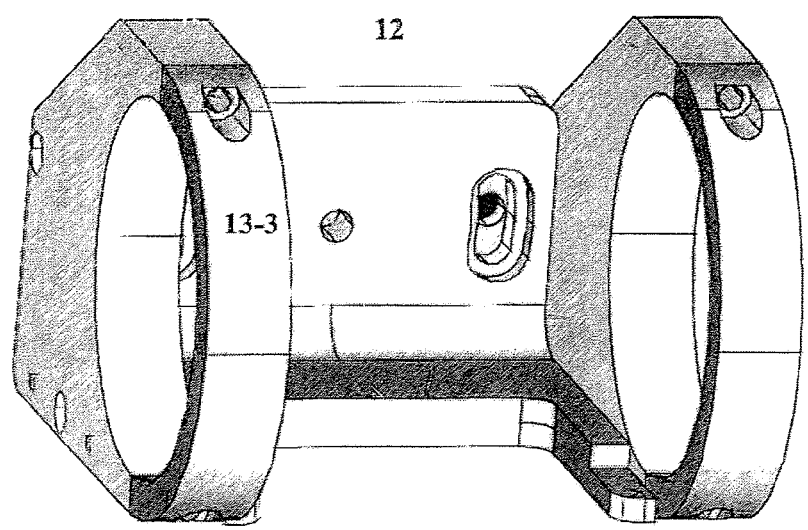
FIG. 5 shows an elevation view of a detail of a mechanical fixing means according to the invention.

FIG. 5 shows that the emitter 13-1 is secured to the support 12 by means of a mechanical fixing means 13-3 having at least one degree of freedom, i.e. allows precisely positioning the emitter 13-1 so that the field of view of the first tomograph 13 is the desired one, i.e. without interferences due to, for example, the second tomograph 14 which is not operating in this moment, and assures the correct perpendicular geometry of the emitter 13-1 and X-ray detector 13-2.

Consequently, while the first tomograph 13 is operating, the second tomograph 14 is not operating, i.e. it is not capturing data, as a result the sampling is sequential and the difference between the sampling of the first tomograph 13 and the second tomograph 14 is as small as desired.

The subject undergoing examination and placed horizontally on the bed is located in the field of view of the first tomograph 13 and second tomograph 14, therefore, said field of view is coincident for both tomographs 13, 14, preventing errors due to sampling in a different field of view, since the subject undergoing examination is not moved. The data capture is very geometrically precise when the field of view coincides for both tomography systems 13, 14.

The second tomograph 14 comprises at least one detector system 14-1 to 14-4, a pair of opposite detectors for the case of PET tomograph, since in this case the emitter source is inside the examined subject to which an emitter substance with predetermined features was administrated. For example, depending on the substance administrated to the examined subject, in the second tomograph 14 a predetermined type of receptor such as PET, SPECT, optical or the like, will be used.

Also, depending on the inner diameter of the inner circumference of the support ring 12, a large number of detectors 14-1 to 14-4, and detector pairs for PET, of the same tomography system or, also, several detectors corresponding to different tomography systems can be installed. Therefore, at least two different tomography systems coexist on the same support 12, so that the number installed depends on the inner diameter of the support ring which in turn is related to the size of the subject to be examined, i.e. if the subject to be examined is a small animal that is used in laboratory studies, then at least two different tomography systems are installed; if the subject to be examined is larger, for example a human being, more than two tomography systems can be installed since the diameter of hole of the support 12 is substantially larger than in the previous case.

In any of the previous cases of different examined subjects, the number of tomography systems also depends on the maximum distance at which the examined subject must be located from any of the elements or components forming the different coplanar tomographs 13, 14. It should be understood that the maximum distance between the subject and any of the tomographs 13, 14 can be different since each tomograph captures data based on different computer assisted tomography techniques.

To prevent intermodal interferences between the first tomograph 13 and the second tomograph or imaging system 14, since different types of radiation coexist simultaneously in the field of view, the tomograph 11 comprises shielding or screening means 16, 17 configured, designed and located to prevent possible interferences of the first tomograph 13 in the second tomograph 14 or vice versa. In the previously described case, the detectors 14-1 to 14-4 of the second tomograph 14 are screened by means of a first screening means 16. The first screen 16 protecting the detectors 14-1, 14-3 has been removed to show the mentioned detectors 14-1, 14-3 of the second tomograph 14.

As can be seen in the mentioned FIG. 2, the upper and lower parts of the first screen 16 have a different geometric shape, since the shape of the mentioned first screen 16 is adapted to the cone-shaped beam 15 of the first X-ray tomograph 13 at the distal end of the emitter 13-1. That is to say, the surface of the mentioned distal end of the first screen 16 is substantially parallel to the cone-shaped beam 15 of the first tomograph 13. The shielding of the detectors 14-1 to 14-4 of the second tomograph 14 is performed such that the effectiveness against scattered radiation is suitable for its correct operation, preventing interference with other imaging modalities such as the first tomograph 13.

Figure 4:
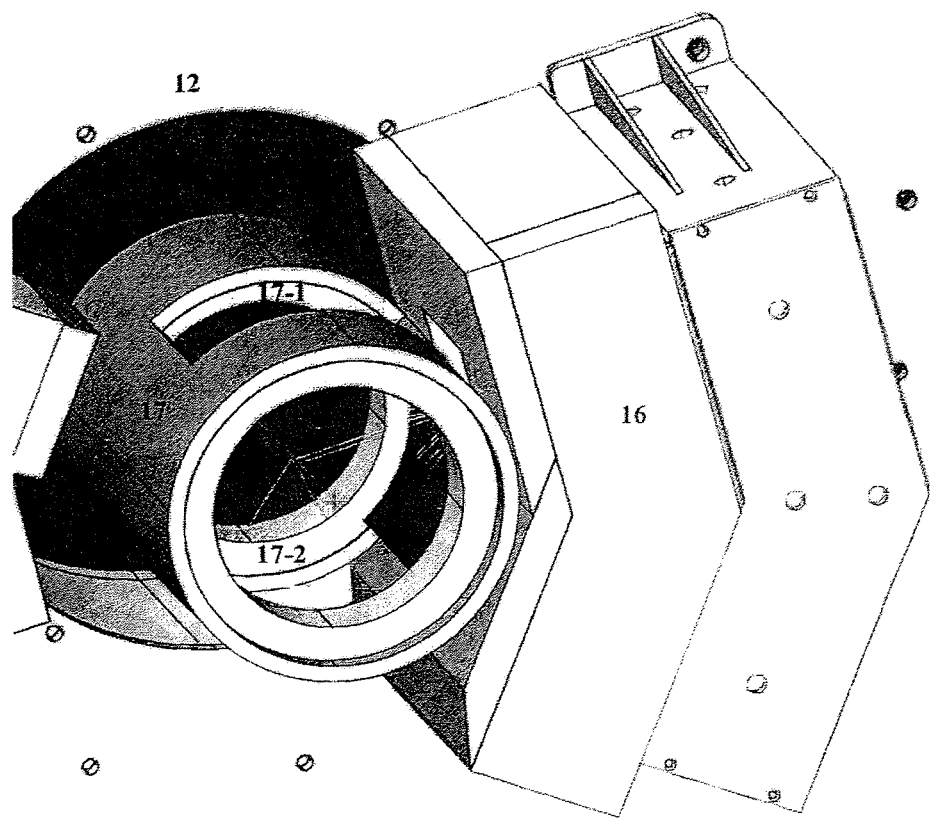
FIG. 4 shows an elevation view of a detail of a second screening means according to the invention.

A second screening means 17 is located in the hole of the support ring 12. The mentioned second screen 17 has a hollow cylindrical shape that is concentric to the inner hole of the support 12. The second screen is housed in said hole of the support 12 and comprises at least two opposite windows 17-1, 17-2, see FIGS. 2 and 4, having predetermined dimensions depending on a cross section of the cone-shaped beam 15. In some cases, said windows 17-1, 17-2 are substantially aligned with the mentioned cone-shaped beam 15 of the first tomograph 13 and in other circumstances, they are not aligned with said cone-shaped beam 15, therefore, it is not possible obtain samplings with the first tomograph 13.

The mentioned second screen 17 can rotate around the axial shaft of the support 12, so that when the first tomograph 13 is not operating, since it is to perform a sampling with the second tomograph 14, the second screen is rotated such that it covers the radiation field 15 between the emitter 13-1 and detector 13-2 corresponding to the first tomograph 13. In this case, the windows are substantially aligned with the detectors 14-1 to 14-4 of the second tomograph 14.

The mentioned second screen 17 is suitable for the case of when the subject undergoing examination is a laboratory animal. However, in that case as well as when the patient subject is a human being, said second screen 17 could include mechanical means with a substantially flat surface installed in front of the first tomograph 13 and the second tomograph 14 performing the same function as the second cylindrical screen 17 previously described. The flat surfaces will be moved from one position in which it cuts the field of view to another position in which it does not cut said field by means of motorized means. In general, the second shielding or screen 17 works as an obturator with circular movements, linear translation or concentric translation. When necessary, it is complemented with mobile obturator type devices, or electromechanical or hydraulic systems that reconfigure the arrangement of these shieldings in real time so that they optimize the operation of the tomograph 11.

Figure 3:
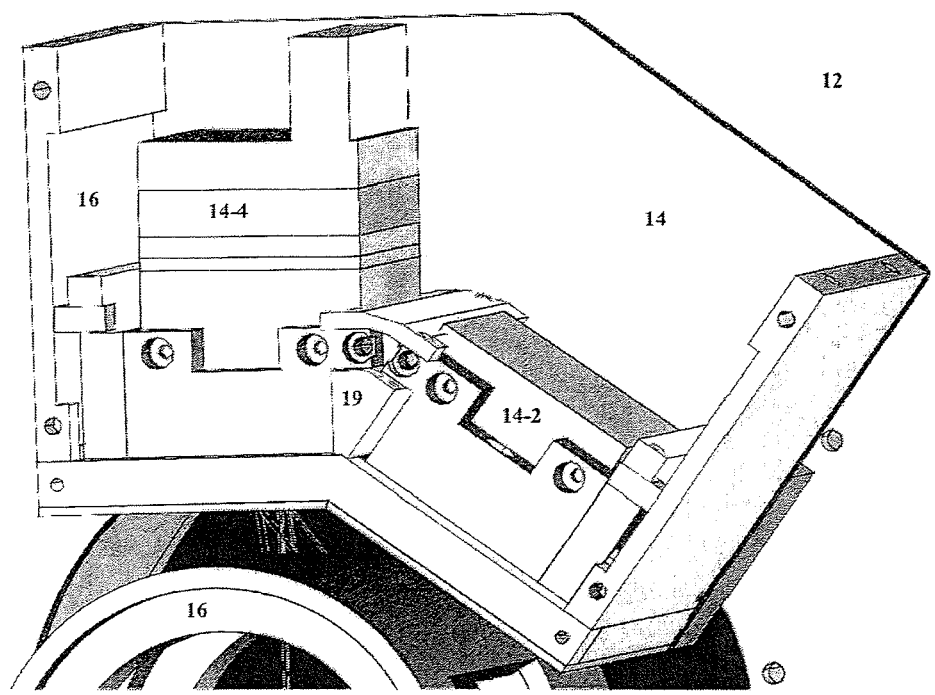
FIG. 3 shows an elevation view of a detail of a second tomograph or imaging system according to the invention.

Now in relation to FIG. 3, two contiguous detectors 14-2, 14-4 of the second tomograph 14 are connected by a wedge-shaped type connection means 19 made in a material of the same density as the scintillation crystal, so that the sensitivity of the second half-ring tomograph 14 increases and, in addition, the wedge 19 maintains the continuity of density in the virtual detector plane such that image reconstruction algorithms based on system models have no discontinuities in the entire second tomograph 14.

The position of detectors 14-1 to 14-4 of the second tomograph or planar imaging system 14 related to the effective field of view is important for conservation of good sensitivity and spatial resolution. Sensitivity is conserved by keeping them close to the useful field of view, but this can interfere with the fields of view of other tomography techniques.

Detectors 14-1 to 14-4 of the second tomograph 14 use flat detectors that intrinsically reduce the parallax error as they cover most of the field of with orthogonal lines, which are those that do not have parallax error. Furthermore, detectors 14-1 to 14-4 of the second tomograph 14 are arranged adjacent such that the virtual detector plane is continuous and larger, increasing the transaxial field of view and at the same time maintaining the orthogonality between the detectors 14-1 to 14-4 of the second tomograph 14.

The invention claimed is:
1. A multi-modality tomography apparatus comprising
   (a) a support ring (12) rotatable around an axial shaft in either of two directions;
   (b) a first computer-assisted tomograph (13) supported on a face of the support ring, said first computer-assisted tomograph emitting radiation in a cone-shaped beam and comprising first tomograph detector means for detecting radiation;
   (c) a second computer-assisted tomograph (14) having a different operating principle from the first tomograph (13) comprising second tomograph detector means for detecting radiation, said second tomograph being supported on the face of the support ring; wherein the first tomograph and the second tomograph are disposed on the face of the support ring in a common plane and such that the first and second tomographs have an overlapping effective field of view whereby each of the first and second tomographs can take image samples of the same region of a subject without moving the subject, and wherein the first tomograph detector means and the second tomograph detector means are spaced from one another in a circumferential direction along the support ring.

2. The apparatus according to claim 1, wherein the at least second tomography comprises a planar imaging system.

3. The apparatus according to claim 1, further comprising a support for horizontal positioning of a subject, the support being movable along the axial shaft of the support ring such that the subject disposed horizontally on the support can be positioned at a set location within the overlapping effective field of view at which each of the first and second tomographs can take image samples of the same region of the subject without moving the subject.

4. The apparatus according to claim 3, wherein the support ring comprises supports for receiving, securing and supporting components of the first and second tomographs.

5. The apparatus according to 4, wherein the first tomograph comprises an emitter and fixing means for movably securing the emitter on the support ring with at least one degree of freedom.

6. The apparatus according to claim 5, wherein the second tomograph detector means comprises at least two opposite and aligned detectors.

7. The apparatus according to claim 6, comprising first means for screening the detectors of the second tomograph from radiation emitted from the emitter of the first tomograph.

8. The apparatus according to claim 7, wherein the first screening means has a surface at a distal extreme that is substantially parallel to the effective field of view of the first tomograph.

9. The apparatus according to claim 1, wherein the second tomograph detector means comprises a plurality of contiguous detectors and wedge-shaped connection means for connecting the plurality of contiguous detectors.

10. The apparatus according to claim 9, wherein the second tomograph comprises a scintillation crystal and the connection means comprises a material of the same density as the scintillation crystal whereby the connection means maintains a continuity of density in a pane defined by the plurality of contiguous detectors.

11. The apparatus according to claim 6, wherein the detectors of the second tomograph comprise flat detectors.

12. The apparatus according to claim 8, wherein the second tomography comprises second means for screening the detectors from radiation emitted from the emitter of the first tomography, said second screening means being rotatable around the axial shaft of the support ring in both clockwise and counterclockwise directions whereby it can be rotated alternatively to block the field of view of either the first or the second tomograph.

13. The apparatus according to claim 12, wherein the second screening means comprises at least two regular polygonal-shaped window openings.

14. The apparatus according to claim 13, wherein the second screening means is a hollow cylinder.

15. The apparatus according to claim 12, wherein the second screening means comprises screens and means for moving the screens between a plurality of different positions whereby to obdurate the field of view of either the first or the second tomograph.

16. The apparatus according to claim 15, wherein the first and second tomographs are adapted for either sequential or simultaneous capturing of data from the overlapping effective field of view.

17. The apparatus according to claim 16, wherein each of the first and second tomographs is selected from the group consisting of X-ray tomographs, positron emission tomographs, single photon emission tomographs and optical imaging techniques.

18. The apparatus according to claim 17, wherein the first tomography is an X-ray tomograph and the second tomograph detector means detects emissions from an emitter source within a subject.

19. The apparatus according to claim 1, wherein the second tomography provides a projective image without being a tomographic image.

20. The apparatus according to claim 1, wherein the first tomograph is an X-ray tomography and comprises a transparent, collapsible, mobile screen with a lead content that protects an operator from X-ray contamination.

21. A multi-modality tomography apparatus comprising:
   (a) a support ring comprising a longitudinal shaft for accommodating a support for a patient; said support ring comprising a face and being rotatable around the longitudinal shaft;
   (b) a first tomograph comprising an emitter that emits radiation in a cone-shaped beam and a detector attached to the face of the support ring; the emitter and detector being disposed along a first axis that is transverse to and intersects the longitudinal shaft;
   (c) a second tomograph comprising means for detecting emissions from an emitter source within the patient when the patient is supported on a support accommodated in the shaft, said second tomograph being attached to the face of the support ring in a common plane with the first tomograph; the means for detecting emissions being disposed in the plane along a second axis that is transverse to and intersects the longitudinal shaft, said second axis being different than the first axis.

22. The apparatus according to claim 21, wherein the second tomograph comprises an optical imaging system.

23. The apparatus according to claim 21, further comprising a support for horizontal positioning of a patient, the support being movable along the longitudinal shaft of the support ring such that the patient disposed horizontally on the support can be positioned at a set location within a field of view at which each of the first and second tomographs can take image samples of the same region of the patient without moving the subject.

24. The apparatus according to claim 21, wherein the first and second axes are orthogonal axes.

25. The apparatus according to claim 1, comprising screening means for screening the second tomograph from radiation emitted from the first tomograph while allowing the cone-shaped beam to pass to the first tomograph detector means when the screening means is aligned with the cone-shaped beam.

26. The apparatus according to claim 21, comprising screening means for screening the second tomograph from radiation emitted from the first tomograph while allowing the cone-shaped beam to pass to the detector of the first tomograph when the screening means is aligned with the cone-shaped beam.

* * * * *